US008852079B2

(12) United States Patent
Sandstrom

(10) Patent No.: US 8,852,079 B2
(45) Date of Patent: Oct. 7, 2014

(54) VALVE ASSEMBLY WITH SHAPE MEMORY MEMBER

(75) Inventor: Jeffrey Sandstrom, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 163 days.

(21) Appl. No.: 13/405,580

(22) Filed: Feb. 27, 2012

(65) Prior Publication Data

US 2013/0221251 A1    Aug. 29, 2013

(51) Int. Cl.
*A61F 2/00* (2006.01)
*A61B 17/02* (2006.01)
*F16K 31/00* (2006.01)

(52) U.S. Cl.
CPC ............ *A61B 17/0218* (2013.01); *F16K 31/002* (2013.01)
USPC ............................................ 600/37; 600/205

(58) Field of Classification Search
CPC ..... A61B 17/02; A61B 17/218; F16K 31/002
USPC ........... 600/37, 210, 201, 205, 206, 214, 215, 600/229; 137/468, 316; 60/527; 251/11, 90, 251/129.01, 129.06
See application file for complete search history.

(56) References Cited

U.S. PATENT DOCUMENTS

| | | | | |
|---|---|---|---|---|
| 4,736,587 A | * | 4/1988 | Suzuki | ............................. 60/528 |
| 4,973,024 A | * | 11/1990 | Homma | ......................... 251/11 |
| 5,211,371 A | * | 5/1993 | Coffee | ............................. 251/11 |
| 5,941,813 A | * | 8/1999 | Sievers et al. | ................... 600/16 |
| 5,984,195 A | | 11/1999 | Benedict | |
| 6,464,629 B1 | | 10/2002 | Boone et al. | |
| 6,602,183 B1 | | 8/2003 | Levi et al. | |
| 6,758,809 B2 | | 7/2004 | Briscoe et al. | |
| 6,837,852 B2 | * | 1/2005 | Wu et al. | ....................... 600/210 |
| 7,399,272 B2 | | 7/2008 | Kim et al. | |
| 8,499,779 B2 | * | 8/2013 | Gillespie | .................... 137/15.18 |
| 2006/0008764 A1 | * | 1/2006 | Abo | ................................ 433/95 |
| 2006/0071088 A1 | | 4/2006 | Adams et al. | |
| 2010/0139785 A1 | * | 6/2010 | Saitoh et al. | ................... 137/468 |
| 2010/0305398 A1 | * | 12/2010 | Olson et al. | ..................... 600/37 |

FOREIGN PATENT DOCUMENTS

EP    1 909 008 A1    9/2008

OTHER PUBLICATIONS

Notification of Transmittal of the International Search Report and the Written Opinion of the International Searching Authority, or the Declaration (PCT/US2013/024055) dated Jul. 23, 2013 (16 pages).

* cited by examiner

*Primary Examiner* — Samuel Gilbert
*Assistant Examiner* — Carrie R Dorna

(57) ABSTRACT

A device includes a conduit utilized for vacuum flow and a valve assembly fluidly coupled with the conduit. The valve assembly includes a valve body defining an opening, a valve member moveable with respect to the valve body, and a shape memory member, wherein the shape memory member operates to actuate the valve member to close the opening upon the shape memory member reaching a transition temperature.

16 Claims, 4 Drawing Sheets

VALVE ASSEMBLY WITH SHAPE MEMORY MEMBER

BACKGROUND

Coronary artery disease remains the leading cause of morbidity and mortality in Western societies. A number of approaches have been developed for treating coronary artery disease. In less severe cases, it is often sufficient to merely treat the symptoms with pharmaceuticals or to treat the underlying causes of the disease with lifestyle modification. In more severe cases, the coronary blockage can be treated endovascularly using techniques such as balloon angioplasty, atherectomy, laser ablation, stents, and the like. In cases where these approaches have failed or are likely to fail, it is often necessary to perform a coronary artery bypass graft procedure.

The coronary artery bypass graft procedure traditionally required a heart-lung or cardiopulmonary bypass. Due to the risks incurred during cardiopulmonary bypass, beating heart bypass surgery techniques have been developed to allow coronary artery bypass without cardiopulmonary bypass. Several systems are presently available which attempt to immobilize epicardial tissue in the immediate vicinity of an anastomosis site through a pressure stabilizer employing a simple mechanical fork. Such a device stabilizes the heart by pressing a fork downwards onto the heart surface. The fork is typically mounted to an elongated shaft, which in turn is typically mounted to a retractor, holding the patient's ribs apart to create an operative window. Angular movement of the shaft relative to the retractor in some cases is accomplished by means of a turret, which may be clamped in its desired rotational position. Longitudinal movement of the shaft relative to the retractor is typically allowed as well, and clamping mechanisms are typically provided to allow clamping of the shaft to the turret and locking of the fork relative to the shaft. Exemplary pressure stabilization devices are disclosed in U.S. Pat. No. 5,876,332, issued to Looney and U.S. Pat. No. 6,036,641, issued to Taylor, et al., both incorporated herein by reference in their entireties.

Suction stabilization systems, such as the Medtronic Octopus® Tissue Stabilizer (available from Medtronic, Inc., Minneapolis, Minn. USA), instead employ a comparatively long, flexible arm carrying a pair of suction paddles or pods at its distal end. During use, the arm is typically secured to a surgical spreader or retractor, holding the patient's ribs apart to create an operative window. The pods are placed on either side of the anastomosis site and suction is applied to grip and immobilize the surface of the heart. Thereafter, tension is applied along the length of the arm to lock the arm in its position and to lock the position of the pods relative to the arm. Medtronic's device is generally disclosed in U.S. Pat. No. 6,464,629, issued on Oct. 15, 2002, for a "Method And Apparatus For Temporarily Immobilizing A Local Area Of Tissue", incorporated herein by reference in its entirety. In this device, a single knob, mounted to the proximal end of the arm, is employed to lock the arm in position and additionally to spread the pods somewhat, slightly stretching the heart's surface to provide additional stabilization of the heart surface. In such devices, adjustment of the shaft relative to the surgical retractor is accomplished by varying the configuration of the flexible shaft, prior to locking it in its desired position. Other examples of suction stabilization devices are disclosed in U.S. Pat. No. 6,113,534, issued to Koros, et al., U.S. Pat. No. 6,007,486, issued to Hunt, et al, U.S. Pat. No. 5,836,311, issued to Borst, et al. and U.S. Pat. No. 5,727,569, issued to Benetti, et al., all incorporated herein by reference in their entireties.

In conjunction with stabilization devices, suction retractors are often employed to position the heart to allow access to the desired anastomosis site. The Medtronic Starfish™ device and the Guidant Axius™ Expose™ device are examples of commercially available suction retractors. These devices employ a single, larger suction pod to engage the heart, typically in the vicinity of the heart apex. The suction pod is carried by a flexible arm, which, like the suction stabilizers discussed above, also may be locked into a desired configuration by tension applied along their length. The application of tension to the arm may also serve to lock a carrier for the suction pod relative to the arm to fix the suction pod in a desired orientation relative to the arm, as in the Guidant device. The Medtronic device is described in U.S. Pat. No. 7,069,241, issued Jun. 27, 2006 for a "Method and System for Unified Management of Plurality of Assets Using Computer Network", incorporated herein by reference in its entirety. The Guidant device is described in the brochure "Axius™ Expose™ Device, Instructions for Use, Guidant Corp., 2001, P/N 30462, Rev. A, also incorporated herein by reference in its entirety. Other suction retractors are described in U.S. Pat. No. 6,019,772, issued to Spence, et al. and PCT Publication No. WO 01/17437 by Peng, both also incorporated herein by reference in their entireties.

Regardless of the particular device utilized, end users often times will attempt to reprocess medical devices for multiple uses. During reprocessing, the device is sterilized, which includes exposing the device to high temperatures, potentially leading to unintended failure of the device. As many medical devices are designed for single use only, patient safety can be compromised when attempting to reuse the device. As such, preventing unauthorized reprocessing of devices would increase patient safety.

SUMMARY

A device includes a conduit utilized for vacuum flow and a valve assembly fluidly coupled with the conduit. The valve assembly includes a valve body defining an opening, a valve member moveable with respect to the valve body, and a shape memory member. The shape memory member operates to actuate the valve member to close the opening upon the shape memory member reaching a transition temperature.

DETAILED DESCRIPTION

Figure 1:
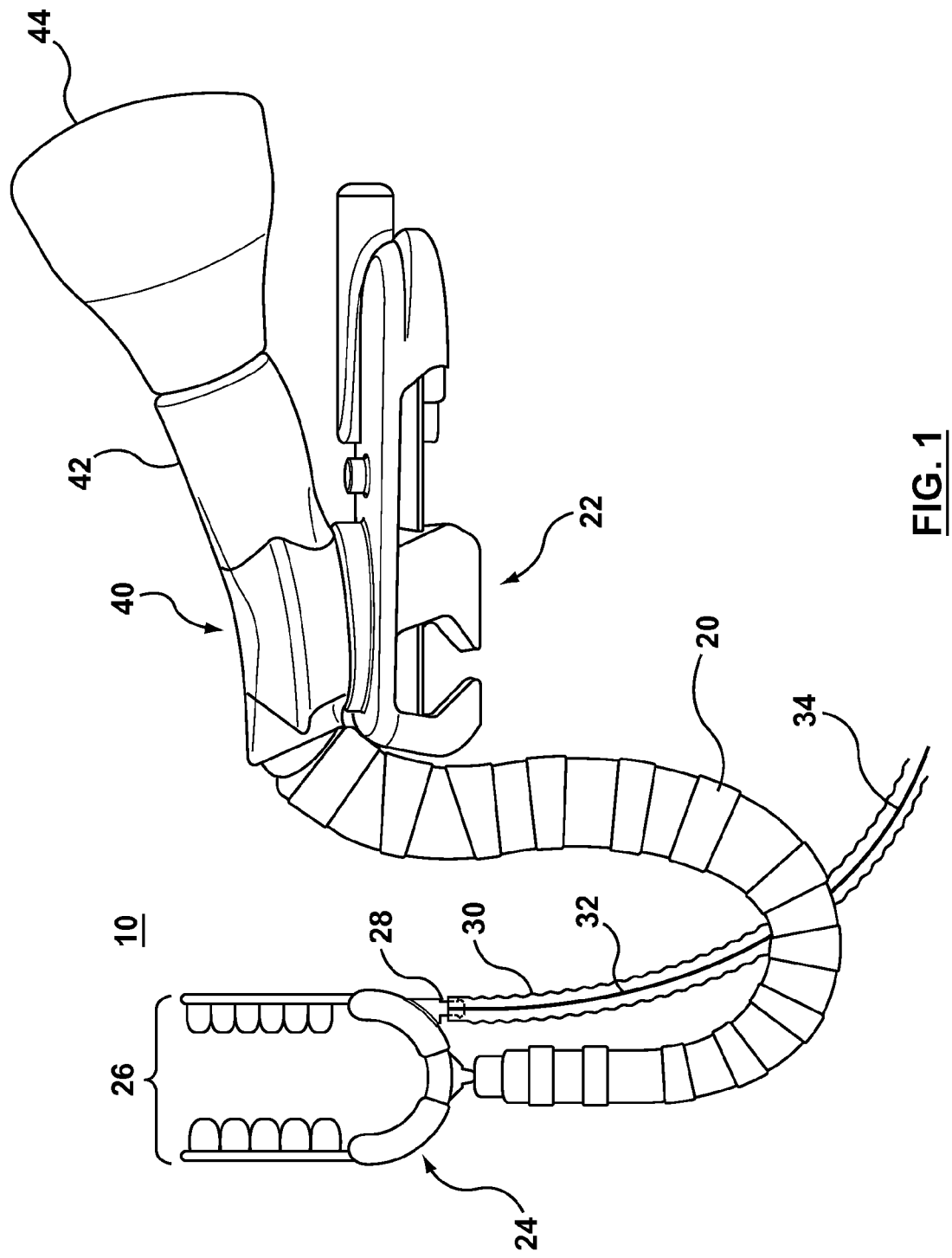
FIG. 1 is a perspective view of a suction stabilizer.

FIG. 1 is a perspective view of an exemplary device 10 that includes a valve assembly to prevent multiple uses of the device 10 in the event the device 10 is subject to sterilization.

To that end, the valve assembly employs a shape memory member configured to shut off a supply of vacuum within the device 10 such that the device 10 will no longer properly function. The shape memory member, when heated during a sterilization process (e.g., to around 40-45° Celsius), transitions to a predetermined, originally forged shape that will shut off vacuum supply within the device 10. To prevent the shape memory member from transitioning to the predetermined shape during an initial sterilization, a plug or other obstruction element is positioned within the valve assembly prior to the initial sterilization. This element is removed prior to use and the valve assembly is otherwise inaccessible such that the element is not replaced within device 10 for further sterilization.

The shape memory member can take many forms and be configured in several different shapes and sizes. In one embodiment the shape memory member is shaped and positioned such that, upon sterilization, the shape memory member returns to a predetermined shape. During the transition, the shape memory member actuates a valve member that shuts off vacuum supply through the valve assembly, rendering the device non-functional for further use. As such, the shape memory member can define a first position, where vacuum is allowed through the valve assembly, and a second position, where vacuum flow through the valve assembly is prevented. In some embodiments, the shape memory member is formed of a suitable shape memory alloy such as nickel-titanium (known as nitinol), copper-zinc-aluminum-nickel, copper aluminum nickel and/or combinations comprising one or more of zinc, copper, gold, iron, nickel and titanium.

In one embodiment, device 10 includes a flexible, articulating distal arm 20 attached to a base assembly 22 at its proximal end and terminates with a headlink 24 including a tightening/spreading mechanism at its distal end. Extending distally beyond headlink 24 is a plurality (as shown, two) of suction paddles or pods 26. The suction pods 26 are connected to a vacuum line by a vacuum line connection 28. Each pod and its suction ports may be constructed in any acceptable manner, such as that used in the Medtronic Octopus™ tissue stabilizer, discussed above.

Vacuum line connection 28 is coupled with a vacuum line tube 30 that delivers vacuum from a remote vacuum source (not shown) to the distal pods 26. As discussed below, connection 28 employs a valve assembly that includes a removable obstruction element coupled to a tether line 32. Prior to use, a user pulls on tether line 32 at a proximal end 34 to remove the obstruction element and tether line 32 from the connection 28 and the tube 30. Once removed, tube 30 can be coupled with a vacuum source to supply vacuum to the pods 26. As such, the pods 26, the vacuum line connection 28 and the tube 30 are all in fluid communication with one another.

To operate stabilizer 10, the proximal end of distal arm 20 is mounted to a turret assembly 40, which allows the proximal end of distal arm 20 to be rotated relative to the base assembly 22 and relative to the surgical retractor to which it is typically attached. A tension member (not shown) passes through the distal arm 20 and through the turret assembly 40 and operates to compress the turret assembly around an associated pivot extending upward from base assembly 22. A tensioning mechanism 42 is allowed to be moved relative to the base assembly 22 using a handle 44 extending from a proximal end of the tensioning mechanism 32 and is operatively coupled to provide tension to the tension member discussed above, which extends from the spreading/tightening mechanism 24, through distal arm 20 and through the turret assembly 40.

Application of tension by means of handle 44 serves to perform multiple functions, including locking the distal arm 20 in its current configurations, rotationally locking the turret assembly 40 relative to the base assembly 22, and activating the spreading/tightening mechanism 24 to spread pods 26 slightly apart from one another. The details of operation of this mechanism are discussed in more detail in commonly assigned U.S. Pat. No. 6,866,628, issued Mar. 15, 2005 for an "Apparatus for Temporarily Engaging Body Tissue", incorporated herein by reference in its entirety.

While one embodiment disclosed herein is practiced in the context of a retractor or stabilizer in which a valve assembly is positioned within headlink 24, other embodiments can usefully practiced in the context of other devices which are not associated with a retractor or stabilizer. In such devices, a suitable valve assembly may be employed to prevent reprocessing of the device 10 as discussed below.

Figure 2:
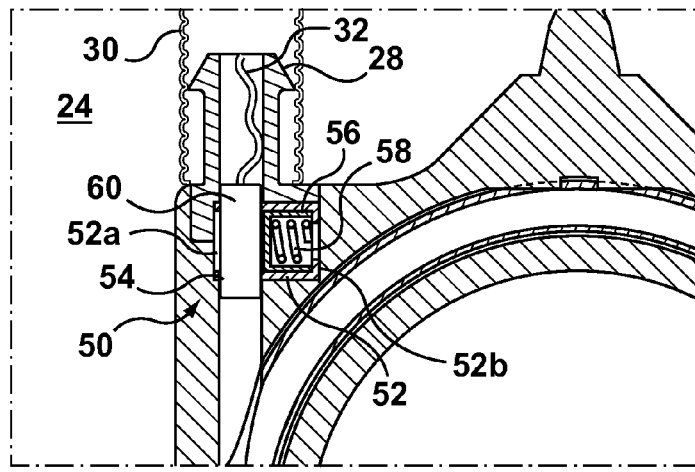
FIGS. 2-4 are sectional view of a headlink employing a valve assembly to prevent use of the stabilizer of FIG. 1 after sterilization.
Figure 3:
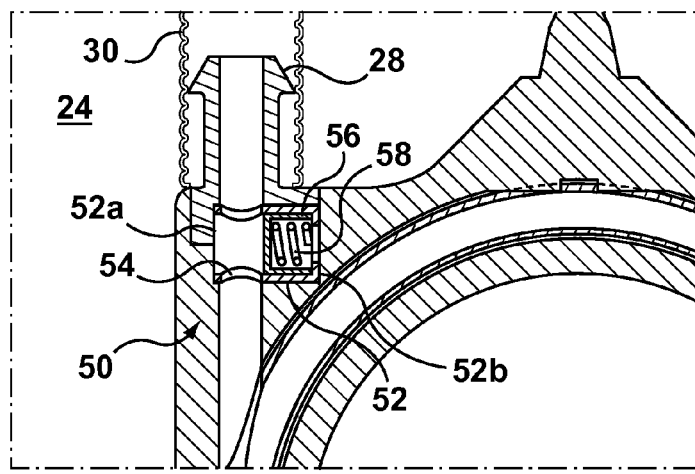
Figure 4:
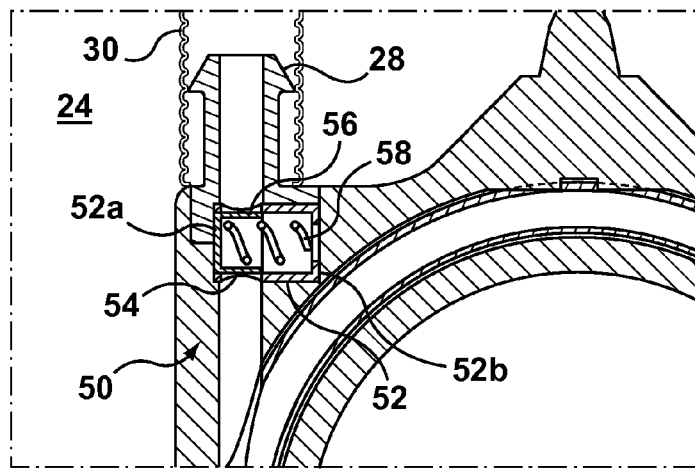

FIGS. 2-4 illustrate schematic, cross-sectional views of headlink 24 as well as vacuum line connection 28 extending therefrom. In order to prevent reuse of the device 10, a valve assembly 50 is disposed within the headlink 24 and fluidly coupled to the vacuum line connection 28 and vacuum line tube 30. The valve assembly 50 includes a valve body 52 defining an opening 54, a valve member 56 and a shape memory member 58. Valve assembly 50 is positioned within the headlink 24 to otherwise be inaccessible without destroying operation of the headlink 24. Although valve body 52 can be formed in various configurations, in the embodiment illustrated, valve body 52 is sealed within headlink 24 by connector 28 and generally includes a first side 52a and a second side 52b.

Prior to sterilization and initial use, a removable obstruction element (herein embodied as a plug) 60 attached to tether line 32 is positioned within the valve assembly 50 as illustrated in FIG. 2. In particular, plug 60 is positioned within the opening 54 of the valve body 52. In order to accommodate the plug 60, valve member 56 and shape memory member 58 are compressed toward the first side 52b of the valve body 52. Shape memory member 58 is embodied as a coil that expands upon reaching a transition temperature. With plug 60 preventing shape memory member 58 from expanding, the device can be sterilized wherein plug 60 prevents shape memory member 58 from moving valve member 56 toward side 52a of valve body 52. In order to use the device, a user (e.g., a surgeon), removes the plug 60 from the opening 54 by pulling on tether line 32, as illustrated in FIG. 3. At this point, vacuum is free to flow through the headlink 24. In the event one attempts to expose the device to a sterilization cycle without the tethered plug 60 in the opening 54, shape memory member 58 returns to an original forged shape (i.e., by expanding), causing valve member 56 to move toward side 52a and close opening 54, as illustrated in FIG. 4.

Figure 5:
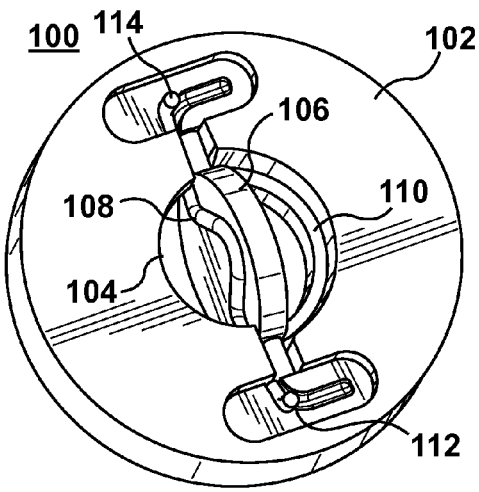
FIGS. 5 and 6 illustrate an alternative valve assembly for use with the stabilizer of FIG. 1.
Figure 6:
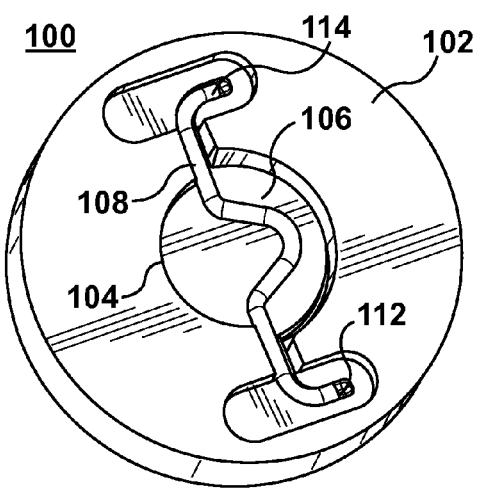

FIGS. 5-13 illustrate alternative valve assemblies that can be used to replace valve assembly 50 illustrated in FIGS. 2-4. FIGS. 5 and 6 illustrate a butterfly type valve 100 including a valve body 102, a valve opening 104, a valve member 106 and a shape memory member 108. In FIG. 5, valve assembly 100 is in an open position whereas in FIG. 6, valve assembly 100 is in a closed position. As shown in the open position of FIG. 5, opening 104 includes a recess 110 designed to interface with valve member 106, which is embodied as a disk. The shape memory member 108 is embodied as a wire, including opposed ends 112 and 114 positioned on either side of the valve opening 104. Moreover, the shape memory member 108 is directly coupled to valve member 106 such that, upon reaching a transition temperature (e.g., by subjecting the valve assembly to sterilization), the shape memory member 108 actuates (i.e., rotates) the valve member 108 to close the valve assembly 100, as shown in FIG. 6. Prior to sterilization, an obstruction element can be positioned within opening 104 on either side of the valve member 106, or on both sides of the valve member 106. After sterilization and prior to use, the element can be removed from the opening 104 such that proper vacuum can be established therethrough. In the event of further sterilization, shape memory member 108 transitions to a predefined shape, operating to close the valve member 106, as shown in FIG. 6. As such, the device would not be functional for further use.

Figure 7:
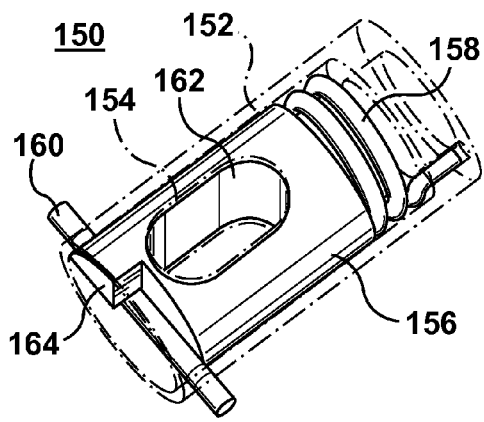
FIGS. 7 and 8 illustrate an alternative valve assembly for use with the stabilizer of FIG. 1.
Figure 8:
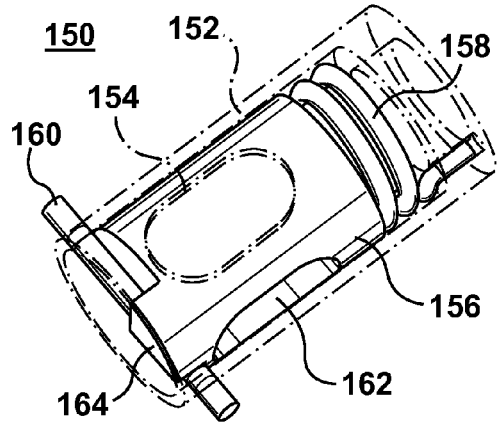

FIGS. 7 and 8 illustrate an alternative valve assembly 150 including a valve body 152 defining an opening 154. Positioned within the valve body 152 are a valve member 156, a shape memory member 158 and an overtravel stop, herein embodied as a pin 160. Shape memory member 158 is coupled to valve member 156 and configured, upon reaching a transition temperature, to actuate (i.e., rotate) the valve member 156. Prior to sterilization, a removable obstruction element (not shown) is positioned within opening 154 such that valve member 156, which includes a corresponding opening 162, is aligned with the opening 154 and is in a first position to allow vacuum flow through valve assembly 150. Prior to use, the element is removed from opening 154. In the event of sterilization, shape memory member 158 transitions to a predefined shape and into a second position, operating to rotate valve member 156 such that a leg portion 164 of valve member 156 contacts pin 160, thus preventing vacuum flow through the opening 154 of valve body 152.

Figure 9:
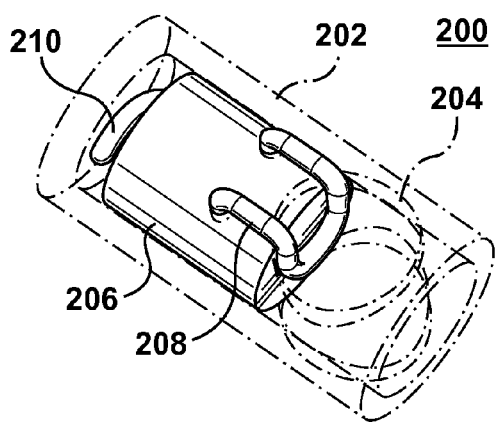
FIGS. 9 and 10 illustrate an alternative valve assembly for use with the stabilizer of FIG. 1.
Figure 10:
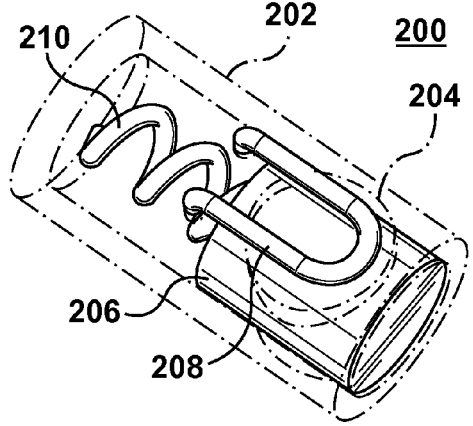

FIGS. 9 and 10 illustrate an alternative valve assembly 200 including a valve body 202 defining an opening 204. Coupled to the valve body 202 are a valve member 206 and a shape memory member 208. A removable obstruction element (not shown) is positioned within opening 204 and shape memory member 208 is folded within the opening 204 as shown in FIG. 9. During sterilization and prior to use, the element is removed so as to allow flow through the opening 204. In the event of sterilization, shape memory member 208 extends such that a biasing member (herein embodied as a spring) 210 acts against valve body 202 to position valve member 206 within the opening 204 as illustrated in FIG. 10.

Figure 11:
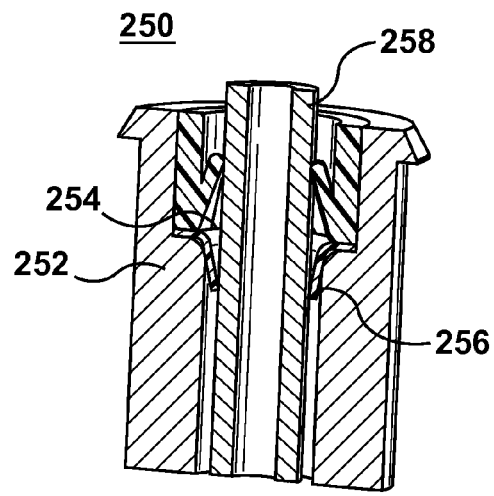
FIGS. 11-13 illustrate an alternative valve assembly for use with the stabilizer of FIG. 1.
Figure 12:
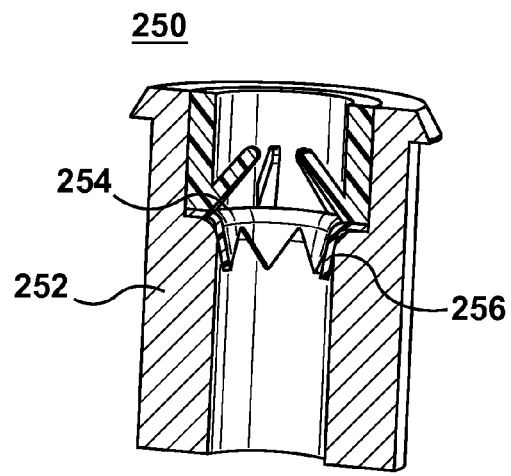
Figure 13:
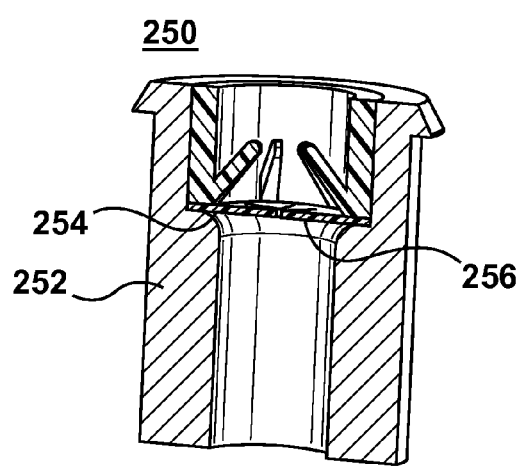

FIGS. 11-13 illustrate an alternative valve assembly 250 including a valve body 252 defining an opening 254 and a valve member 256 positioned within the valve body 252. A removable obstruction element 258 is positioned within the valve body 252 during initial sterilization so as to prevent valve member 256 from closing the opening 254 of valve body 252. Prior to use, element 258 is removed from the valve body 252 as illustrated in FIG. 12. In the event of sterilization and as illustrated in FIG. 13, valve member 256 operates to close the opening 254, rendering the device 10 not functional for its intended use.

Although the present disclosure has been described with reference to preferred embodiments, workers skilled in the art will recognize that changes can be made in form and detail without departing from the spirit and scope of the present disclosure.

What is claimed is:

1. A device, comprising:
   a conduit utilized for vacuum flow; and
   a valve assembly fluidly coupled with the conduit, comprising:
      a valve body defining an opening,
      a valve member movable with respect to the valve body,
      a shape memory member, and
      an obstruction element positioned with the opening such that the shape memory member is prevented from closing the opening upon the shape memory member reaching a transition temperature, wherein the shape memory member operates to actuate the valve member to close the opening upon removal of the obstruction element and the shape memory member reaching the transition temperature so as to maintain the valve member in a closed position when the device returns below the transition temperature.

2. The device of claim 1, wherein the shape memory member is a coil that expands to actuate the valve member upon reaching the transition temperature.

3. The device of claim 1, wherein the valve member comprises a disk and the shape memory member operates to rotate the disk upon reaching the transition temperature.

4. The device of claim 1, wherein the valve member includes a valve member opening that is movable between a first position, wherein the valve member opening fluidly communicates with the opening of the valve body and a second position, wherein the valve member opening is positioned such that the opening of the valve body is blocked.

5. The device of claim 1, wherein the valve assembly further includes a biasing member coupled to the shape memory member and the valve member such that the shape memory member prevents the biasing member from biasing the valve member to a closed position, and further wherein, upon the shape memory member reaching the transition temperature, the shape memory member is positioned such that the biasing member acts to close the opening with the valve member.

6. A method of preventing multiple uses of a single use medical device, comprising:
   positioning a removable obstruction element within an opening of a valve assembly fluidly coupled with a conduit utilized for vacuum flow, the valve assembly including a valve body defining the opening, a valve member movable with respect to the valve body and a shape memory member, the shape memory member operable to actuate the valve member to close the opening upon the shape memory reaching a transition temperature; and
   sterilizing the device such that the obstruction element remains within the opening so as to prevent the shape memory member from operating to actuate the valve member to close the valve opening.

7. The method of claim 6, wherein the shape memory member is a coil that expands to actuate the valve member upon reaching the transition temperature.

8. The method of claim 6, wherein the valve member comprises a disk and the shape memory member operates to rotate the disk upon reaching the transition temperature.

9. The method of claim 6, wherein the valve member includes a valve member opening that is movable between a first position, wherein the valve member opening fluidly communicates with the opening of the valve body and a second position, wherein the valve member opening is positioned such that the opening of the valve body is blocked.

10. The method of claim 6, wherein the valve assembly further includes a biasing member coupled to the shape memory member and the valve member such that the shape memory member prevents the biasing member from biasing the valve member to a closed position, and further wherein, upon the shape memory member reaching the transition temperature, the shape memory member is positioned such that the biasing member acts to close the opening with the valve member.

11. The method of claim 6, further comprising removing the obstruction element positioned with the opening such that the shape memory member operates to close the valve opening upon the shape memory member reaching the transition temperature.

12. A suction stabilizer, comprising:
a base assembly;
an articulating arm coupled to the base assembly;
a headlink coupled to the arm and including:
    a plurality of pods at a distal end of the headlink,
    a vacuum line connection fluidly coupled to the plurality of pods, and positioned in the headlink the vacuum line connection further coupleable with a tube extending to a vacuum source, and
    a valve assembly positioned within the vacuum line connection, wherein the pods, the vacuum line connection, the tube and the valve assembly are fluidly coupled to one another with the vacuum line connection fluidly positioned between the tube and the valve assembly, the valve assembly including:
        a valve body defining an opening,
        a valve member movable with respect to the valve body, and
        a shape memory member,
    an obstruction element positioned with the opening such that the shape memory member is prevented from closing the valve opening upon the shape memory member reaching a transition temperature, wherein the shape memory member operates to actuate the valve member to close the opening upon removal of the obstruction element and the shape memory member reaching the transition temperature.

13. The stabilizer of claim 12, wherein the shape memory member is a coil that expands to actuate the valve member upon reaching the transition temperature.

14. The stabilizer of claim 12, wherein the valve member comprises a disk and the shape memory member operates to rotate the disk upon reaching the transition temperature.

15. The stabilizer of claim 12, wherein the valve member includes a valve member opening that is movable between a first position, wherein the valve member opening fluidly communicates with the opening of the valve body and a second position, wherein the valve member opening is positioned such that the opening of the valve body is blocked.

16. The stabilizer of claim 12, wherein the valve assembly further includes a biasing member coupled to the shape memory member and the valve member such that the shape memory member prevents the biasing member from biasing the valve member to a closed position, and further wherein, upon the shape memory member reaching the transition temperature, the shape memory member is positioned such that the biasing member acts to close the opening with the valve member.

* * * * *

UNITED STATES PATENT AND TRADEMARK OFFICE
CERTIFICATE OF CORRECTION

| | | |
|---|---|---|
| PATENT NO. | : 8,852,079 B2 | Page 1 of 1 |
| APPLICATION NO. | : 13/405580 | |
| DATED | : October 7, 2014 | |
| INVENTOR(S) | : Jeffrey Sandstrom | |

It is certified that error appears in the above-identified patent and that said Letters Patent is hereby corrected as shown below:

In The Claims

In Claim 1, column 5, line 61
"reaching a transition temperature, wherein" should read -- reaching the transition temperature, wherein --

In Claim 6, column 6, line 39
"memory reaching a transition temperature;" should read -- memory reaching the transition temperature; --

In Claim 12, column 7, line 10
"and positioned in the headlink the vacuum" should read -- and positioned in the headlink, the vacuum --

In Claim 12, column 7, lines 26, 27
"reaching a transition temperature, wherein" should read -- reaching the transition temperature, wherein --

Signed and Sealed this
Twenty-second Day of September, 2015

Michelle K. Lee
*Director of the United States Patent and Trademark Office*